United States Patent [19]

Doi et al.

[11] 4,370,301

[45] Jan. 25, 1983

[54] DRY DEODORIZING APPARATUS

[75] Inventors: Kunihiro Doi; Tetsu Takeyama, both of Amagasaki; Kenkoku Azuma, Nagoya, all of Japan

[73] Assignee: Mitsubishi Denki Kabushiki Kaisha, Tokyo, Japan

[21] Appl. No.: 211,286

[22] Filed: Nov. 28, 1980

[30] Foreign Application Priority Data

Nov. 28, 1979 [JP] Japan ............................. 54-154099
Jul. 31, 1980 [JP] Japan ............................. 55-105792
Jul. 31, 1980 [JP] Japan ............................. 55-105793
Jul. 31, 1980 [JP] Japan ............................. 55-105794

[51] Int. Cl.³ .................. A61L 9/015; A61L 9/00; A61L 9/16
[52] U.S. Cl. .................................. 422/122; 422/3; 422/4; 422/5; 422/31
[58] Field of Search .............. 422/3, 4, 5, 37, 31, 422/122; 62/78

[56] References Cited

U.S. PATENT DOCUMENTS 3,969,479 7/1976 Lonnes et al. .................. 422/4 X
4,256,710 3/1981 Azuma et al. .................. 422/4 X
4,256,728 3/1981 Nishino et al. .................. 422/4

FOREIGN PATENT DOCUMENTS 50-131847 10/1975 Japan .
54-132470 10/1979 Japan .
55-34137 3/1980 Japan .................................. 422/4
55-20732 6/1980 Japan .

*Primary Examiner*—Barry S. Richman
*Attorney, Agent, or Firm*—Oblon, Fisher, Spivak, McClelland & Maier

[57] ABSTRACT

A dry deodorizing apparatus. More particularly, it relates to a dry deodorizing apparatus wherein bad smell components in the gas to be treated is oxidized and removed by ozone and bromine and hydrobromine acid and, in addition, the ozonizing material such as ozone and bromine entrained by the air to be treated is removed with an adsorbent or a decomposing agent so that no secondary environmental pollution due to ozonizing material takes place.

18 Claims, 11 Drawing Figures

DRY DEODORIZING APPARATUS

BACKGROUND OF THE INVENTION

1. Field of the Invention

The present invention relates to a dry deodorizing apparatus.

2. Description of the Prior Art

Heretofore, a dry deodorizing apparatus using activated carbon shown in FIG. 1 has been used.

In FIG. 1, the reference numeral (1) designates a blower; (2) designates an adsorption column and (3) designates a layer of activated carbon packed in the adsorption column (2). The air to be treated (A) having bad smell is fed into the adsorption column (2) by the blower (1), the main part of the bad smell components is adsorbed and removed principally by the physical adsorption and partly by the chemical adsorption and the like by the metal components contained in the activated carbon as impurities (ash) while the air is allowed to pass through the activated carbon layer (3) and it is discharged therefrom as the treated air (B). In such an apparatus, the deodorization performance depends upon the physical adsorption capacity of the activated carbon; for instance, in order to remove a moderately bad smell compound such as methyl sulfide or dimethyl disulfide which is a typical bad smell component or a component such as ammonia whose amount adsorbed by the activated carbon is small and whose adsorption band is wide, a satisfactory deodorization effect can not be obtained so far as a large amount of activated carbon is not accordingly, there are many cases wherein the practice is economically difficult.

Also there is disclosed a deodorizing method in which, as shown in Japanese Unexamined Patent Publication No. 130679/1975, an impregnated activated carbon which is prepared by allowing the activated carbon to carry bromine or a bromine compound is used to remove hydrogen sulfide or mercaptans. However, when the removal capacity is increased by an additional oxidation removal step wherein ozone is added to the air to be treated, particularly when the concentration of hydrogen sulfide in the air to be treated is high, the residual ozone and bromine leak because they are entrapped by the treated gas.

SUMMARY OF THE INVENTION

It is therefore, an object of the present invention to provide a dry deodorizing apparatus which removes the defect of an activated carbon adsorption process using a conventional apparatus or a deodorization process wherein an activated carbon which carries bromine or a bromine compound is used.

Other objects of the present invention are to provide a dry deodorizing apparatus having a high deodorization capacity in spite of a small amount of the activated carbon used for adsorbing and removing ozone and bromine which remains in and leak together with the treated gas; to provide a dry deodorizing apparatus which causes no secondary environmental pollution due to the residual ozone and gaseous bromine; to provide a dry deodorizing apparatus which effectively remove acidic bad smell gases by oxidation decomposition and to provide a dry deodorizing apparatus which extends the life of oxidation reaction due to ozone and an impregnated activated carbon which carries hydrogen bromide or hydrobromic acid and, in addition, has a high efficiency to remove hydrogen sulfide.

A further object of the present invention is to provide a dry deodorizing apparatus which can effectively remove the components such as ammonia, methyl sulfide and dimethyl disulfide which can not be easily removed by an adsorption process using an activated carbon.

DETAILED DESCRIPTION OF THE PREFERRED EMBODIMENT

Figure 1:
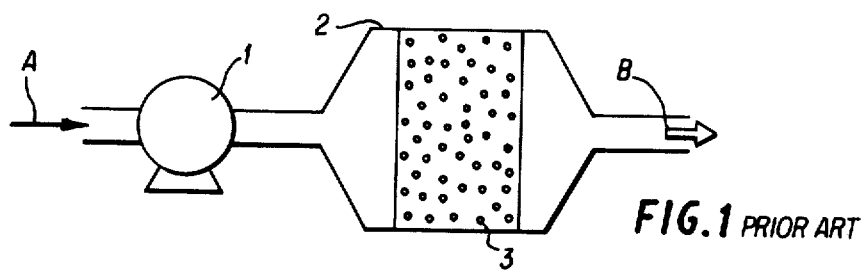
FIG. 1 is a flow diagram of the conventional dry deodorizing apparatus using an activated carbon.
Figure 2:
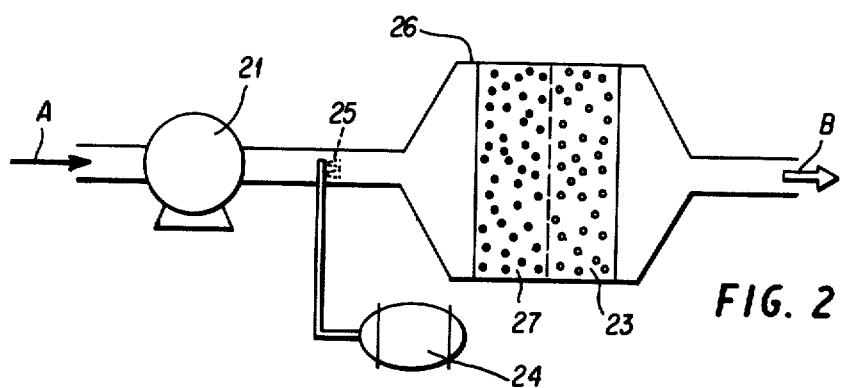
FIG. 2 is a flow diagram of an apparatus in one of the embodiments of the present invention.

FIG. 2 is a flow diagram according to an apparatus of one of the embodiments of the present invention. This dry deodorizing apparatus has a high deodorization performance in spite of a small amount of the activated carbon used by adding ozone to the air to be treated, allowing this air to be treated to contact the hydrogen bromide or hydrobromic acid-impregnated porous material to cause oxidation and decomposition of bad smell components and adsorbing and removing ozone and bromine contained in the air by allowing the treated air to pass through the layer of an activated carbon.

In FIG. 2, the reference numeral (21) designates a blower; (23) designates a layer of an activated carbon; (24) designates an ozonizer; (25) designates a diffuser tube of the ozonized air; (26) designates a reaction column and (27) designates a packed layer of an impregnated porous material consisting of a carrier such as alumina which carries hydrogen bromide or the solution thereof. In the apparatus having such a constitution, the air to be treated suctioned by the blower (21) is mixed with the ozonized air fed from the ozonizer (24)

through the diffuser tube (25) and the mixture passes through the packed layer of the impregnated porous material (27) in the reaction column (26). In this process, ozone and hydrogen bromide or hydrobromic acid (hereinafter the both compounds are abbreviated to HBr) are allowed to rapidly react to produce bromine or hydrobromic acid (hereinafter referring to $Br_2$, HBrO) in accordance with the reaction formula (1) and and (2) mentioned below; $Br_2$ and HBrO contact and oxidize the bed smell components on the surface of the impregnated porous material and, at the same time, an oxidation reaction occurs also in the gas phase resulting in the oxidation and the removal of bad smell components.

$$2HBr + O_3 \rightarrow Br_2 + H_2O + O_2 \quad (1)$$

$$HBr + O_3 \rightarrow HBrO + O_2 \text{ (in } H_2O) \quad (2)$$

In the next step, the air to be treated which passed through the packed layer of the impregnated porous material (27) enters the layer of the activated carbon (23) wherein the residual ozone and $Br_2$ in the air are adsorbed, ozone is reduced to oxygen, the bad smell components are removed and the air being free of substances which cause the secondary environmental pollution is discharged out of the system as the treated air B.

The outline of the constitution of the present invention is as stated above and now the detailed description on the reaction with bad smell components and the effect thereof are given hereinbelow.

As a bromide other than HBr which reacts with ozone to produce $Br_2$, there can be illustrated a compound such as potassium bromide or ammonium bromides. However, the present invention is based upon the findings that the compound which can effectively produce Br or HBrO in the reaction with ozone is HBr. The said oxidation reaction with bromine thus produced is effective against methyl sulfide or dimethyl disulfide which shows low removal performance when an activated carbon is used. Also a basic bad smell component such as ammonia or trimethylamine can be removed by the neutralization reaction with HBr. The materials used for adsorption which have a low iron content, e.g. alumina, silica-alumina, activated clay, activated carbon and the like can easily impregnate HBr. Typical examples of the reaction formulae of various reactions such as neutralization gas phase and contact oxidation and the like in the apparatus of the present invention may be represented by the following equations (3)–(8):

$$NH_3 + HBr \longrightarrow NH_4Br \quad (3)$$

$$2NH_3 + 3Br_2 \longrightarrow N_2 + 6HBr \quad (4)$$

$$(CH_3)_3N + HBr \longrightarrow (CH_3)_3N \cdot HBr \quad (5)$$

$$(CH_3)_3N + Br_2 \xrightarrow{H_2O} (CH_3)_3NO + 2HBr \quad (6)$$

$$(CH_3)_2S + Br_2 \xrightarrow{H_2O} (CH_3)_2SO + 2HBr \quad (7)$$

-continued $$(CH_3)_2S_2 + Br_2 \xrightarrow{H_2O} CH_3S\underset{\underset{O}{\|}}{S}CH_3 + 2HBr \quad (8)$$

Figure 3:
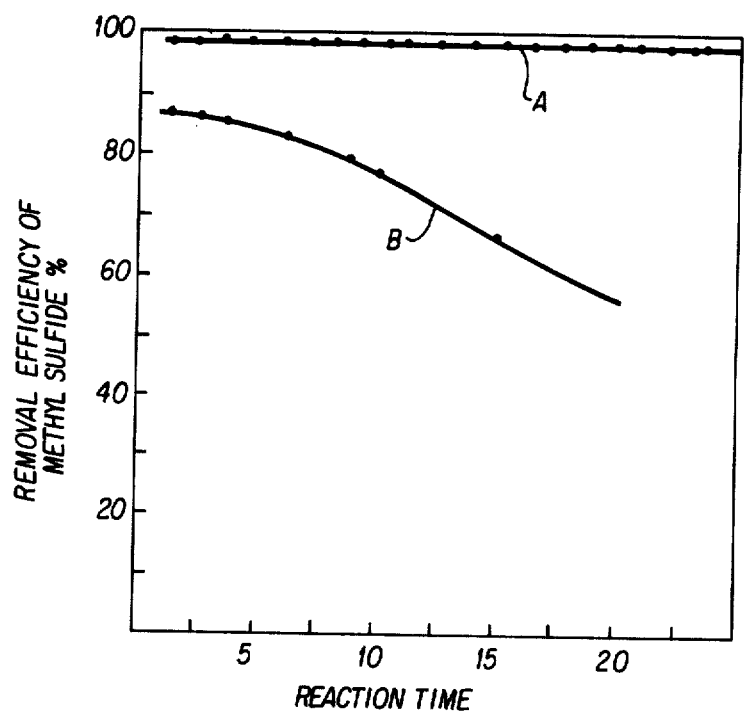
FIG. 3 is a diagram to illustrate the capacity to treat methyl sulfide when the apparatus of the embodiment shown in FIG. 2 is used.

FIG. 3 is a diagram to illustrate the result when methyl sulfide, a typical bad smell component, is treated; the abscissa shows the reaction time and the ordinate the removal efficiency (%) of methyl sulfide. When the air which contains 2.7 ppm of methyl sulfide and 10–11 ppm of ozone is allowed to pass through the reaction tube having a diameter of 40 mm packed with alumina having a size of 4–6 meshes (pore volume: 0.43 ml/g, specific surface area: 140 m²/g) so that the thickness of the layer thereof reaches 40 mm at a rate of 10 l/min. (space velocity: approximately 24,000 hr$^{-1}$), the removal of methyl sulfide at the position of the layer thickness of 20 mm is shown by the characteristic curve A and, for comparison, the results obtained when the same mixture of air was allowed to pass through the tube under the same conditions is shown by the characteristic curve B. That is, in this diagram, the characteristic curve A shows that the removal of methyl sulfide is maintained at levels higher than 98.5% even after the operation for 10 hours; on the other hand, the characteristic curve B shows the removal lower than 80% after the operation for 10 hours though the initial removal was 87%.

The rate constant of the gas phase reaction of ozone and methyl sulfide is approximately $8 \times 10^7$ m³/kg-mol.hr. Consequently, when the reaction was allowed to occur under said conditions for 5 seconds, the removal of methyl sulfide is 5% at best and a gas phase oxidation reaction of it with ozone can not be expected. Accordingly, the removal of methyl sulfide using an HBr-impregnated porous material and ozone is based upon the oxidation reactions of bromine produced in accordance with the reaction formula (1) or hydrobromine acid, reaction formula (2) and the bed smell components which occur in the gas phase and on the surface of the carrier. The effect was particularly remarkable in the case of dimethyl sulfide.

Figure 4:
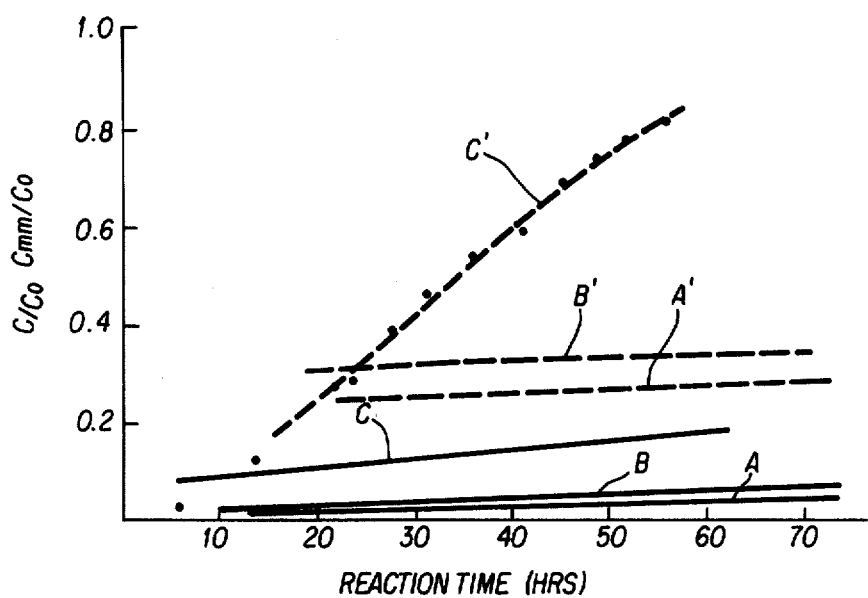
FIG. 4 is a diagram to illustrate the capacity to treat methyl mercaptan and dimethyl disulfide when the apparatus of the embodiment in FIG. 2 is used.

FIG. 4 is a diagram to illustrate the results obtained when methyl mercaptan, a typical bad smell component along with dimethylsulfide, is treated. The air containing 2.33 ppm of mercaptan and 10–11 ppm of ozone is allowed to pass through the reaction tube having a diameter of 40 mm in which HBr-impregnated porous material was packed to form a layer of 20 mm thickness at a rate of 10 l/min. The leakage ratio $C/C_o$ (concentration at outlet/concentration at inlet) when an activated clay was used as the carrier is shown by the characteristic curve A, and that when alumina was used is shown by the characteristic curve B. In addition, the characteristic curve C shows for comparison the case wherein an activated carbon which does not impregnate HBr is used.

Further, the characteristic curves A', B' and C' represent the change of the ratio $C_{MM}/C_o$ with time which elapsed wherein $C_{MM}$ is the concentration of dimethyl disulfide at the outlet calculated as that of methyl mercaptan (the value when it is assumed that 1 mol of dimethyl disulfide is produced from 2 mols of methyl mercaptan) and $C_o$ is the concentration of methyl mercaptan at the inlet when an activated clay, alumina and an activated carbon which does not impregnate any material are used as the carrier, respectively.

As known from the characteristic curves A, B and C, the performance to remove methyl mercaptan when an HBr-impregnated porous material is used is superior to that when a nonimpregnated activated carbon is used. That is, even after 55 hours, a high removal efficiency of 95% was maintained in the former case. Also, as shown from the characteristic curves A', B' and C', in the case of dimethyl disulfide, approximately 80% of it was discharged after 55 hours when a nonimpregnated activated carbon was used; on the contrary, less than 35% of it was discharged when an impregnated porous material was used; in addition, the change of leakage ratio with time which elapsed was small and it has been known that its outstanding removal performance was revealed.

Hereinafter the results of ammonia removal obtained when the atmosphere of a trickling filter type clarification tank is used for the treatment of domestic waste water using the deodorizing apparatus of the present invention will be mentioned. Table 1 shows the conditions of the treatment and Table 2, the results obtained.

TABLE 1

| Air to be treated | 0.1m³/min. |
|---|---|
| Amount of ozone added | 3.5ppm on the basis of the air to be treated |
| Contact time | 0.37 sec., with the hydrobromic acid-impregnated porous material |
| Hydrobromic acid-impregnated porous material | carrier: alumina (carrying hydrobromic acid by 3% as bromine) thickness of the layer: 100mm |
| Activated carbon | thickness of the layer: 50mm |

TABLE 2

| Operation time (hr.) | 18–51 | 150–184 | 950–1000 |
|---|---|---|---|
| Odor concentration before treatment/after treatment | 411–1700 | 273–1300 | 330–1500 |
|  | 13–20 | 9.7–26 | 7.3–25 |
| Ammonia (ppm) | less than 0.32–0.63/0.09 | | |

Herein the concentration of odor was determined by sensory test (triangle test) and the concentration of ammonia was determined by indophenol method. It has been made clear from the Table that the performance to remove ammonia of the deodorizing apparatus of the present invention is not decreased after the continuous operation for 1000 hours and a reliable deodorization effect can be obtained based on the observation of odor concentration.

The HBr-impregnated porous material used in these experiments was prepared by immersing each carrier in a 10% aqueous solution of hydrobromic acid for 1 hour and drying it in the atmosphere of nitrogen. A 10% aqueous solution of hydrobromic acid has a vapor pressure as low as $4 \times 10^{-4}$ mmHg and almost no stimulative odor, its handling is easy and the evaporation of hydrogen bromide in the atmosphere of nitrogen when dried is little. However, when an aqueous solution of hydrobromic acid having a concentration higher than 30% is used for the preparation of a hydrobromic acid-impregnated porous material, the evaporation of hydrogen bromide due to drying is remarkably much causing an uneconomical result. The amount of hydrobromic acid impregnated by various carriers and calculated as bromine when a 10% aqueous solution of hydrobromic acid was used is represented as the weight percent per unit weight of each carrier and it was 0.8–1.5% in the case of an activated carbon, 4.8–5% in the case of an activated clay and 2.5–3% in the case of alumina.

In addition, hydrogen bromide is also impregnated together with hydrobromic acid by the impregnated porous material thus prepared and a similar impregnated porous material can be obtained by allowing a gas which contains hydrogen bromide to pass through it instead of using an aqueous solution of hydrobromic acid.

In the embodiment mentioned above, an activated clay and alumina are used as the carrier; however, the application of the procedure is not limited to those in this embodiment but the procedure can be applied to silica-alumina, zeolite, bentonite and the like and, further, to an activated carbon.

As known from the detailed description mentioned above, in the present invention there are provided an ozonizer, a device to allow the ozonized gas to diffuse into the air to be treated having bad smell components, a packed layer of an impregnated porous material consisting of a carrier into which hydrogen bromide or hydrobromic acid is impregnated, a packed layer of an activated carbon and a blower which makes the air to be treated to which ozone is added pass through said packed layer of the impregnated porous material and the said packed layer of activated carbon in this order. Thus the bad smell components can be oxidized and removed by the hydrobromic acid or bromine produced by the reaction of ozone and hydrogen bromide or hydrobromic acid; accordingly, the components which can be hardly adsorbed and removed by an activated carbon can be effectively removed in accordance with the present invention.

Figure 5:
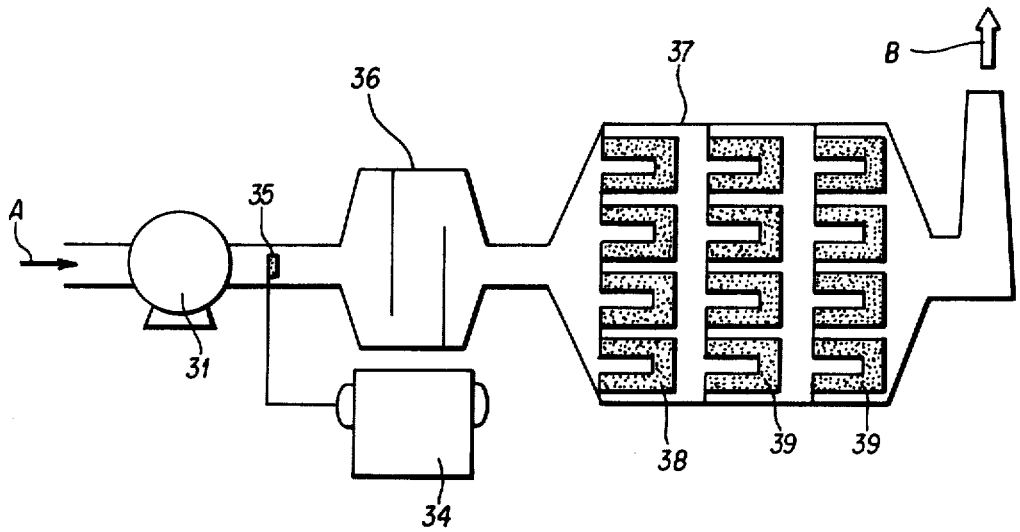
FIG. 5 is a flow diagram of an apparatus according to an other embodiment of the present invention.

FIG. 5 is a flow diagram of an apparatus in other embodiment of the present invention. In accordance with FIG. 5, a deodorizing apparatus having a high deodorization performance in spite of small amount of an impregnated porous material used is prepared by adding ozone to the air to be treated, allowing this air to be treated to contact the hydrogen bromide or hydrobromic acid-impregnated porous material to oxidize and decompose the bad smell components and allowing the air to be treated to pass through the layer of an alkali metal or an alkali earth metal iodide-impregnated porous material to remove the excess ozone and the bromine which leaked resulting in the production of an active iodine (hereinafter it is abbreviated to $I_2$) which serves to cause further oxidation and decomposition of the bad smell components.

In FIG. 5, the reference numeral (31) designates a blower; (34) designates an ozonizer; (35) designates a diffuser tube for ozonized air; (36) designates an ozone mixing tank; (37) designates a reaction column; (38) designates a packed layer of an impregnated porous material consisting of a carrier such as alumina or an activated carbon into which hydrogen bromide or an aqueous solution thereof is impregnated (HBr-impregnated porous material) and (39) designates a packed layer of an impregnated porous material consisting of an activated carbon into which an aqueous solution of potassium iodide is impregnated (KI-impregnated porous material). In an apparatus having such a constitution, the air to be treated A having bad smell suctioned by the blower (31) is mixed with the ozonized air fed from the ozonizer (34) and diffused from the diffuser tube (35) while they pass through the ozone mixing tank (36), then the mixture enters the reaction column (37) and at first pass through the packed tank of HBr-impregnated porous material (38). In this process, as in the case of the apparatus in the embodiment shown in FIG. 2, the bad smell components contact and are oxidized on the surface of the impregnated porous material by the bromine (hereinafter it is abbreviated to $Br_2$) produced by the rapid reaction of ozone and HBr in accordance with the reaction formula (1) and also an oxidation reaction occurs in the gas phase resulting in the oxidation and the removal of the bad smell components.

The air treated which passed through the packed layer of HBr-impregnated porous material (38) is then allowed to pass through the packed layer of KI-impregnated porous material (39). In this process, a very small amount of ozone and $Br_2$ which remain in the air react with KI in accordance with the reaction formulae (11) and (12)

$$O_3 + 2KI + H_2O \rightarrow 2KOH + I_2 + O_2 \qquad (11)$$

$$Br_2 + 2KI \rightarrow 2KBr + I_2 \qquad (12)$$

to produce $I_2$ on the surface of the impregnated porous material. Since this $I_2$ serves as an oxidizing agent, the bad smell components which did not react are oxidized and decomposed; thus, the air is discharged out of the system as a clean air.

The outline of the constitution of the apparatus in the embodiment of the present invention is as stated above and now the detailed description on the reaction with bad smell components and the effect thereof will be given hereinbelow.

The reactions and the like considered to occur at the layer of HBr-impregnated porous material (38) in the apparatus in the embodiment shown in FIG. 5 are similar to those in the case of the apparatus in the embodiment shown in FIG. 2. The present apparatus in the embodiment is proposed based upon the finding that the performance to remove $H_2S$ is improved by further addition of bromine or ozone to the layer of KI-impregnated porous material.

The characteristics shown when methyl sulfide or methyl mercaptan is treated in the layer of HBr-impregnated porous material in the apparatus of this embodiment are similar to those shown in FIG. 3 and FIG. 4.

In the next step, in the layer of KI-impregnated porous material (39), a very small amount of ozone and $Br_2$ which remain in the air which passed through the layer of HBr-impregnated porous material react with KI to easily isolate $I_2$ in accordance with said reaction formulae (11) and (12), and the activated carbon itself becomes basic. Hydrogen sulfide, methyl mercaptan and the like which are acidic gases are not easily removed in the layer of HBr-impregnated porous material; however, they are easily chemically adsorbed by a basic activated carbon and easily react with $I_2$ isolated in accordance with the reaction formulae (13) and (14) producing sulfur and are easily removed.

$$H_2S + I_2 \rightarrow 2HI + S \qquad (13)$$

$$CH_3SH + I_2 \rightarrow CH_3I + HI + S \qquad (14)$$

Figure 6:
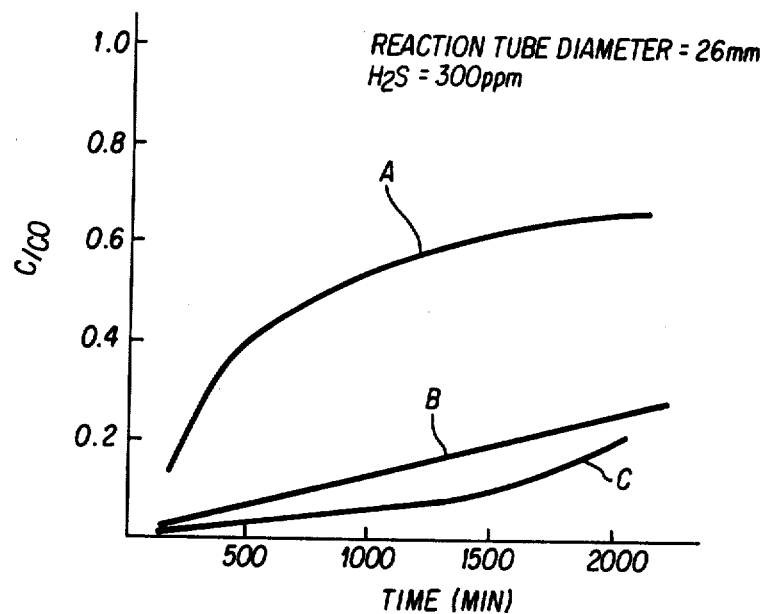
FIG. 6 is a diagram to illustrate the capacity to treat hydrogen sulfide at the layer of sodium iodide impregnated porous material in the apparatus of the embodiment shown in FIG. 5.

FIG. 6 is a diagram to illustrate the results when hydrogen sulfide is treated with KI-impregnated activated carbon. This is a diagram of a characteristic to illustrate the change of leakage ratio $C/C_o$ ($C_o$: concentration at inlet, C: concentration at outlet) of hydrogen sulfide with time which elapsed when an air containing 30 ppm of hydrogen sulfide is allowed to pass, at a flow rate of 10 l/min., through the reaction tube having a diameter of 26 mm in which an activated carbon which has a size of 8-10 meshes and into which KI is impregnated or not impregnated is packed to form a layer having a thickness of 50 mm. The characteristic curve A shows the case of a nonimpregnated carbon and B shows the case of KI-impregnated activated carbon. The characteristic curve C shows the result when an air containing 30 ppm of hydrogen sulfide and 30 ppm of ozone is allowed to pass through the KI-impregnated activated carbon. The leakage ratio after the air was allowed to flow for approximately 30 hours was 65% in the case of nonimpregnated activated carbon, 22.5% in the case of KI-impregnated activated carbon and 18% in the case of KI-impregnated activated carbon plus addition of ozone; thus, the highest performance to remove hydrogen sulfide was obtained when the air to which ozone was added was allowed to pass through the KI-impregnated activated carbon.

Consequently, according to this embodiment in which the layer of KI-impregnated material was provided after the layer of HBr-impregnated porous material, the hydrogen sulfide which leaked from the layer of HBr-impregnated porous material (38) is effectively removed in the layer of KI-impregnated porous material (39) by the synergism of residual ozone and KI-impregnated porous material and a deodorizing apparatus having high performances can be thus constituted.

The preparation of HBr-impregnated porous material in the apparatus of this embodiment is similar to that shown in FIG. 2. Though it is preferable to prepare HBr-impregnated activated carbon using an aqueous solution of hydrobromic acid having a concentration of approximately 10%, a performance which causes no trouble in practice was obtained when a 2% solution was used.

In the embodiment mentioned above an activated clay and alumina were used for the carrier; however, the application is not limited to this example but silica-alumina, zeolite, bentonite, etc. can be used for the carrier. The KI-impregnated activated carbon was prepared by immersing crushed coconut shell activated carbon in a 4% aqueous solution of potassium iodide for 30 minutes and then drying in nitrogen gas. The amount of iodine impregnated was 0.9% as $I_2$. When an aqueous solution of KI having a concentration higher than 20% is used, the cost of chemicals exceeds 50% of the cost of the impregnated activated carbon resulting in an economical problem; accordingly, it is desirable that the impregnation ratio is in a range of 0.5-5%. The amount impregnated was determined by immersing the KI impregnated activated carbon in hot water to extract iodide and then titrating it in accordance with mercuric nitrate method.

Herein the effect of KI-impregnated activated carbon was explained; however, similar effect is revealed when an alkali metal or an alkali earth metal iodide is used.

Now, KI-impregnated activated carbon has been used for a long time as an agent to adsorb and remove radioactive iodine because it has a large capacity to adsorb $I_2$. Consequently, there is little possibility to cause the leakage of excess $I_2$; however, a layer of an activated carbon or an alkali-impregnated porous material may be provided in the latter step of the KI-impregnated activated carbon for the purpose of a countermeasure against the leakage of excess $I_2$ along with the removal of the reaction products such as sulfur dioxide. When the concentration of hydrogen sulfide in the gas to be treated is low, there can be adopted a constitution wherein an air containing ozone and bad smell components is allowed to pass through the layer of HBr-impregnated porous material, the layer of activated carbon and the layer of KI-impregnated porous material in this order.

The apparatus of this embodiment consists of, as mentioned above, an ozonizer; a device to diffuse the ozonized air fed from this ozonizer into the air to be treated containing bad smell components; a packed layer of impregnated porous material consisting of a carrier into which hydrogen bromide or hydrobromic acid is impregnated; a packed layer of an impregnated porous material consisting of a carrier into which an iodide of alkali metal or alkali earth metal is impregnated and a device to send air so that the air to be treated to which said ozone is added passes through said layer of HBr-impregnated porous material and then said layer of iodide-impregnated porous material in this order. Thus, the bad smell components can be oxidized and removed by bromine produced by the reaction of ozone and hydrogen bromide or hydrobromic acid; consequently, the components such as ammonia, dimethyl sulfide and dimethyl disulfide which are not easily removed by an activated carbon can be effectively removed. Further, the residual ozone and bromine in the air treated are removed by allowing them to pass through the layer of iodide-impregnated material and, at the same time, the iodide is oxidized to produce $I_2$ which serves to effectively remove acidic bad smell gases such as hydrogen sulfide and methyl mercaptan causing no secondary environmental pollution; accordingly, its effect in practice is outstanding.

Figure 7:
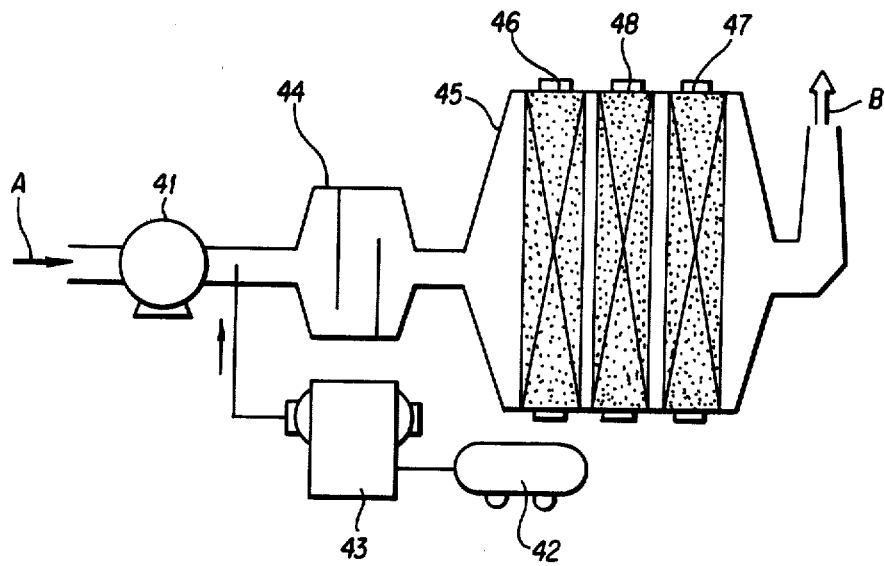
FIG. 7 is a flow diagram of an apparatus according to an other embodiment of the present invention.

Further, an apparatus of an other embodiment of the present invention is shown in FIG. 7. In this apparatus, an acidic gas such as hydrogen sulfide which is not easily adsorbed by the apparatus of the embodiment shown in FIG. 2 can be adsorbed. That is, in the apparatus of the embodiment shown in FIG. 2, in order to adsorb an acidic gas such as hydrogen sulfide, the reaction of it with bromine was necessary; consequently, it was required to increase the amount of ozone added or to increase the amount of the activated carbon packed in the latter step of the activated carbon layer (23) in order to absorb the hydrogen sulfide which is not treated yet. When hydrogen sulfide contained in the gas to be treated A is oxidized in the layer of HBr-impregnated activated carbon (27), sulfuric acid was finally produced; since HBr is an acid weaker than this sulfuric acid, it is replaced with sulfuric acid being gradually transferred from the inlet side to the outlet side of the gas to be treated A and discharged finally into the atmosphere and this causes a problem that the amount of bromine decreased rapidly resulting in its short life.

In the apparatus of the embodiment shown in FIG. 7, a packed layer of an impregnated porous material consisting of a carrier such as activated carbon into which an alkali metal or an alkali earth metal bromide is impregnated (hereinafter it is abbreviated to KBr-impregnated activated carbon) is provided in the down stream of the packed layer of HBr-impregnated porous material so that the HBr diffused from the packed layer of HBr-impregnated activated carbon into the air is seized by this layer and, at the same time, the bad smell components are oxidized and decomposed by the oxidizing action of $Br_2$ in this packed layer.

In FIG. 7, the reference numeral (41) designates a blower; (42) designates a compressor; (43) designates an ozonizer; (44) designates a mixing tank in which the air to be treated suctioned by the blower (41) and the ozonized air fed from the ozonizer (41) are mixed; (45) designates a reaction column; (46) designates a packed layer of an activated carbon into which hydrogen bromide or hydrobromic acid is impregnated (hereinafter it is abbreviated to HBr-impregnated activated carbon); (47) designates a packed layer of an activated carbon and (48) designates a packed layer of KBr-impregnated activated carbon.

Hereafter a description on the action of the apparatus of this embodiment will be given. The air to be treated (A) containing bad smell gases suctioned by the blower (41) is uniformly mixed with the ozonized air fed from the ozonizer (43) while they pass through the mixing tank (43) and then the mixture is introduced into the reaction column (45). The greater part of the bad smell components are removed by the oxidation reaction similar to conventional ones in the packed layer of HBr-impregnated activated carbon (46) in the reaction column (45). Hydrogen bromide is, in accordance with the reaction formulae (21) and (22), decomposed by the oxidation reaction with ozone or $Br_2$ produced in accordance with reaction formula (1), and a part thereof is oxidized finally to sulfuric acid in accordance with the reaction formulae (23) and (24).

$$H_2S + O_3 \rightarrow H_2O + SO_2 \tag{21}$$

$$H_2S + Br_2 \rightarrow 2HBr + S \tag{22}$$

$$SO_2 + H_2O + O_3 \rightarrow H_2SO_4 + O_2 \tag{23}$$

$$SO_2 + H_2O + \tfrac{1}{2}O_2 \rightarrow H_2SO_4 \tag{24}$$

Owing to the accumulation of sulfuric acid produced, the packed layer of HBr-impregnated activated carbon (46) becomes strongly acidic gradually increasing from the side of inlet of the treated air. HBr, which is a weak acid is replaced with $H_2SO_4$ and allowed to move to the side of outlet and gradually leaks from the packed layer of HBr-impregnated activated carbon (46). Under such conditions, the leakage of ozone becomes remarkable.

Then the gas treated which passed through the packed layer of HBr-impregnated activated carbon (46) passes through the packed layer of KBr-impregnated activated carbon (48) and at first potassium hydroxide and bromine are produced in accordance with the reaction formula (25).

$$2KBr + O_3 + H_2O \rightarrow 2KOH + Br_2 + O_2 \tag{25}$$

Potassium hydroxide produced seizes HBr or $H_2S$ in accordance with the reaction formulae (26) and (27).

$$KOH + HBr \rightarrow KBr + H_2O \tag{26}$$

$$KOH + H_2S \rightarrow KHS + H_2O \tag{27}$$

Potassium hydroxide further reacts with bromine to produce sulfur and further deodorization takes place. [reaction formula (28)]

$$KHS + Br_2 \rightarrow KBr + HBr + S \tag{28}$$

Thus, when a packed layer of KBr-impregnated activated carbon is provided, the HBr which leaked can be seized resulting in not only an extension of the life of the performance to oxidize and remove the bad smell components by the reaction of ozone and HBr but also an improvement of, at the same time, the performance to oxidize hydrogen sulfide. In this case, if only a packed layer of KBr-impregnated activated carbon is provided without providing a packed layer of HBr-impregnated activated carbon, then the lowering of the performance of initial deodorization can not be avoided because the reaction to easily produce $Br_2$ in accordance with the reaction formula (1) lacks.

The air to be treated is finally allowed to pass through the packed layer of an activated carbon wherein the reaction products such as excess oxidizing agent and sulfur dioxide are adsorbed and removed and the air is discharged out of the system as the treated air (B).

The constitution of the apparatus of this embodiment is outlined above and hereafter the detailed description of the reaction with bad smell components and the effect thereof will be given. This embodiment is considered to be based upon the findings that, as a bromide, other than HBr, which reacts with ozone to produce $Br_2$, sodium bromide, ammonium bromide, magnesium bromide and calcium bromide can be mentioned. However, one which particularly effectively produces bromine by the reaction with ozone is HBr. When a combination of an HBr-impregnated activated carbon and a potassium bromide or calcium bromide-impregnated activated carbon is used, the decrease in the amount of bromine ion impregnated is controlled and the performance of oxidation can be maintained for a long time.

Figure 8:
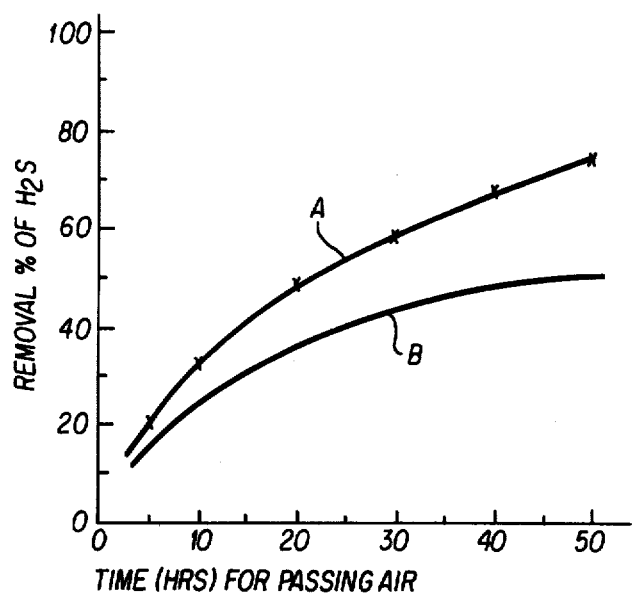
FIG. 8 is a diagram to illustrate the effect on removing hydrogen sulfide when the apparatus of an embodiment shown in FIG. 7 is used.
Figure 9:
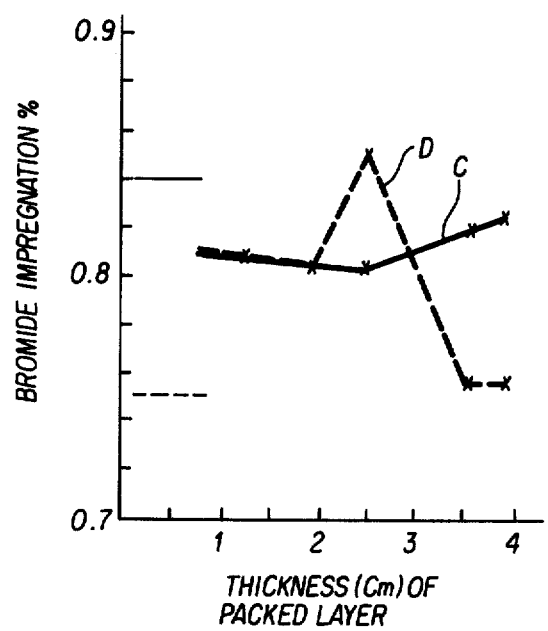
FIG. 9 is a diagram to illustrate the change of the bromine-impregnation ratio on the thickness of the layer in the apparatus of the embodiment shown in FIG. 7.

FIG. 8 is a diagram to show the removal effect when hydrogen sulfide, which is a typical bad smell component, was treated. It is a diagram which shows the change in the removal of hydrogen sulfide with time which elapsed when two reaction columns each having a diameter of $26\phi$ were prepared. An HBr-impregnated activated carbon having a size of 8-10 meshes being packed in one of the columns by 4 cm in height, an HBr-impregnated activated carbon having the same size being packed at first by 2 cm in height and then a KBr-impregnated activated carbon being packed on it by 2 cm in height so that the total height reaches 4 cm in the other column, an air to be treated containing 30 ppm of hydrogen sulfide and 30 ppm of ozone being treated by allowing it to pass through the columns at a flow rate of 10 l/min. for 50 hours. The characteristic curve A shows the case wherein only an HBr-impregnated activated carbon was packed and the characteristic curve B shows that the case wherein an HBr-impregnated activated carbon and a KBr-impregnated activated carbon were packed. The case wherein the combination of an HBr-impregnated activated carbon and a KBr-impregnated activated carbon was used was more effective. Further, after said experiment was carried out, an air containing 3 ppm of dimethyl sulfide and 30 ppm of ozone was allowed to pass through each column for 1 hour and the removal of dimethyl sulfide was determined. As the result, the removals higher than 99% were shown in both cases and it was thus confirmed that the original removal performance was not lowered. FIG. 9 shows the results when the relationship between the thickness of the packed layer of the impregnated activated carbon used for these experiments from the inlet side of the gas to be treated and the bromine impregnation ratio was determined. As an HBr-impregnated activated carbon, one which impregnates HBr of approximately 0.84% as bromine was used and, as a KBr-impregnated activated carbon, one which imprengates KBr of 0.755% as Br was used. In this diagram, the characteristic curve C of solid line represents the case wherein an HBr-impregnated carbon was packed and the characteristic curve D of the broken line represents the case wherein the packed layer of the KBr-impregnated carbon having a height of 2 cm was placed on the packed layer of the HBr-impregnated activated carbon having a height of 2 cm. In the former case, the bromine impregnation ratio was decreased from 0.84% to 0.8-0.81%; however, in the latter case, though the bromine impregnation ratio was decreased similarly in the part of the HBr-impregnated activated carbon, it was increased to 0.85% in the inlet part of KBr-impregnated activated carbon and the pH was decreased. It is considered that this is due to that the HBr discharged from the packed layer of the HBr-impregnated activated carbon was adsorbed and retained by the part of packed KBr-impregnated activated carbon. That is, it is considered that the apparent movement of HBr was restrained and HBr moved more slowly compared with the case wherein only an HBr-impregnated activated carbon was used.

The KBr-impregnated activated carbon was, owing to the economical reason, prepared with an aqueous solution of KBr having a concentration lower than 15% (2-15%) in accordance with the treatment similar to that of HBr-impregnated activated carbon. The appropriate amount of KBr impregnated was 0.5-5% as bromine. Herein the case of a KBr-impregnated activated carbon was mentioned; however, an alkali metal or an alkali earth metal bromide such as NaBr, $CaBr_2$ or $MgBr_2$ reveals the effect of the same extent.

Herein an activated carbon was used for the final packed layer in the reaction column of the deodorizing apparatus; however, there can be used an alkali-impregnated porous material prepared by allowing a carrier such as an activated carbon, zeolite or alumina to impregnate an alkali metal or an alkali earth metal hydroxide or carbonate or an impregnated porous material such as, as far as economically allowed, a KI-impregnated activated carbon which can remove excess oxidizing agent and sulfur dioxide which is a reaction product.

As mentioned above in detail, in this embodiment there are provided an ozonizer, a device to diffuse the ozonized air fed from the ozonizer into the air to be treated containing bad smell components, a packed layer of an impregnated porous material prepared by allowing a carrier to impregnate an alkali metal or an alkali earth metal bromide, a packed layer of an activated carbon or an alkali-impregnated porous material and a device to send air which allows the air to be treated to which ozone was added to pass through said packed layer of HBr-impregnated porous material, the layer of KBr-impregnated porous material and the layer of activated carbon in this order. The apparatus can effectively remove the components such as ammonia, dimethyl sulfide and dimethyl disulfide which can not be easily adsorbed and removed by an activated carbon since the bad smell components are oxidized by bromine produced by the reaction of ozone and hydrogen bromide or hydrobromic acid.

Also HBr which leaks from the packed layer of HBr-impregnated activated carbon is seized by allowing it to pass through the layer of KBr-impregnated porous material and this HBr is effectively utilized; consequently, the life of the oxidation reaction due to said ozone and HBr is extended and, at the same time, the efficiency to remove hydrogen sulfide is raised up. In addition, no secondary environmental pollution takes place since the excess oxidizing agent and the reaction products are adsorbed and removed by the packed layer of alkali-impregnated porous material.

Figure 10:
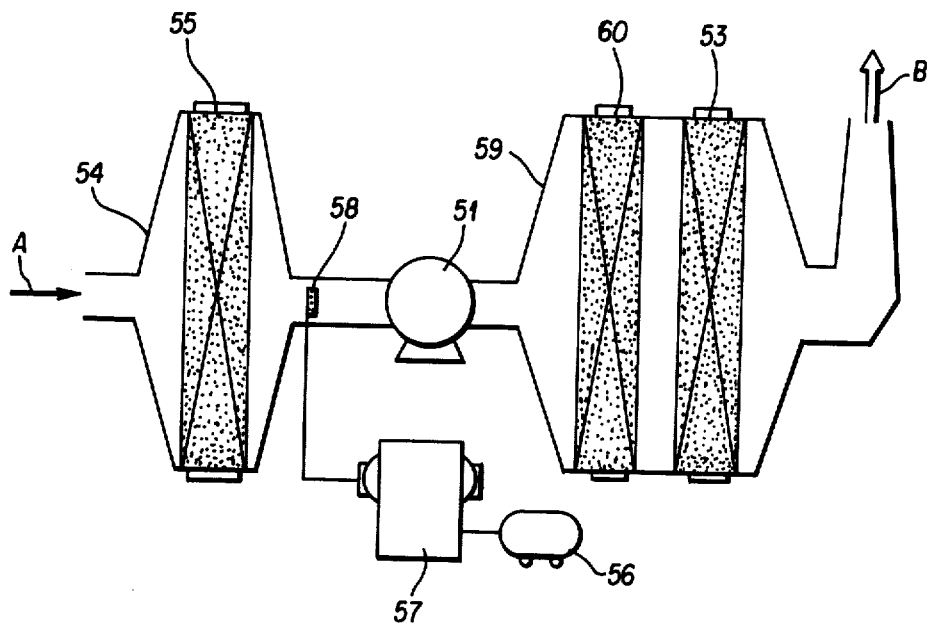
FIG. 10 is a flow diagram of an apparatus according to an other embodiment of the present invention.

An apparatus of an other embodiment of the present invention is shown in FIG. 10. In this apparatus, an air to be treated is at first allowed to pass through the packed layer of an impregnated porous material prepared by allowing a carrier such as an activated carbon, an activated clay, silica-alumina or alumina to impregnate an alkali metal or an alkaliearth metal iodide (hereinafter it is abbreviated to $I_2$-impregnated porous material) to remove bad smell component such as hydrogen sulfide and methyl mercapatan. Then Ozone is added to this treated gas and it is allowed to contact an impregnated porous material prepared by allowing a carrier such as an activated carbon, an activated clay, silica-alumina or alumina to impregnate hydrogen bromide or hydrobromic acid to oxidize and decompose the bad smell components. Further, this treated air is allowed to pass through the layer of an activated carbon or a layer of an alkali-impregnated porous material to remove excess ozone and bromine contained in the air.

In FIG. 10, the reference numeral (51) designates a blower; (53) designates a layer of an activated carbon; (54) designates desulfurizing column; (55) designated a packed tank of $I_2$-impregnated porous material (for instance, a KI-impregnated activated carbon is packed); (56) designates a compressor; (57) designates an ozonizer; (58) designates a diffuser tube; (59) designates a deodorizing tower and (60) designates a packed layer of an HBr-impregnated porous material (for instance, an HBr-impregnated activated carbon is packed). Hereafter the action of the apparatus will be explained. An air to be treated (A) suctioned by the blower (51) is allowed to contact the KI-impregnated activated carbon in the desulfurizing column (54) so that acidic gases such as hydrogen sulfide and methyl mercaptan are removed by adsorption or reaction.

Air was allowed continuously to pass through an impregnated activated carbon prepared by allowing an activated carbon to impregnate KI of approximately 1% as $I_2$ at a rate of SV3000/hr. for 40 hours, then the pH of the impregnated activated carbon was determined in accordance with the test method for granular activated carbon (JIS-1474); as the result, pH was raised up from 9.6 to 10.2. It is presumed that this phenomenon takes place owing to the production of iodine (hereinafter it is abbreviated to $I_2$) and potassium hydroxide in accordance with the reaction formula (31) and it is considered that acidic components such as hydrogen sulfide and methyl mercaptan are removed by these products in accordance with the reaction formulae (32), (33) and (34).

$$2KI + O_2 + H_2O \rightarrow 2KOH + I_2 + \tfrac{1}{2}O_2 \tag{31}$$

$$H_2S + KOH \rightarrow KHS + H_2O \tag{32}$$

$$H_2S + I_2 \rightarrow 2HI + S \tag{33}$$

$$CH_3SH + I_2 \rightarrow CH_3I + HI + S \tag{34}$$

Thus, the greater part of hydrogen sulfide and methyl mercaptan in the air to be treated is removed; an ozonized air is added through the diffuser tube (58) to this treated gas and they are mixed while they pass through the blower (51) and are introduced into the deodorizing tower (59). The air at first passes through the packed layer of HBr-impregnated porous material (60) in the deodorizing tower (59). In this process, the bad smell components contact the surface of the impregnated porous material and are oxidized by the bromine (hereinafter it is abbreviated to $Br_2$) produced by the rapid reaction of ozone and HBr in accordance with the reaction formula (35) and an oxidation reaction takes place at the same time in the gas phase; thus the bad smell components are oxidized and removed.

$$2HBr + O_3 \rightarrow Br_2 + H_2O + O_2 \tag{35}$$

Then the air to be treated which passed through the packed layer of HBr-impregnated porous material (60) is introduced into the packed layer of an activated carbon wherein ozone and $Br_2$ which remain in the air are adsorbed thereby and ozone is reduced to oxygen. The air treated from which the bad smell components and the material to cause the secondary environmental pollution such as an oxdizing agent are removed is discharged out of the system as a cleaned air B.

The outline of the apparatus of this embodiment is as mentioned above and now the detailed explanation on the reaction with bad smell components and the effect thereof will be given hereinbelow.

This deodorizing apparatus reveals the effect particularly in the treatment of the bad smell air containing hydrogen sulfide of high concentration. When the bad smell gas to which ozone was added is allowed to pass through an HBr-impregnated activated carbon, hydrogen sulfide is oxidized to produce sulfuric acid on the surface of the impregnated activated carbon; HBr is turned out by replacement adsorption resulting in a lowering of the amount of HBr impregnated and a decrease of deodorization performance owing to the suppression of the reaction to produce $Br_2$ in accordance with the reaction formula (35). This tendency is remarkable in the case of hydrogen sulfide of high concentration.

Figure 11:
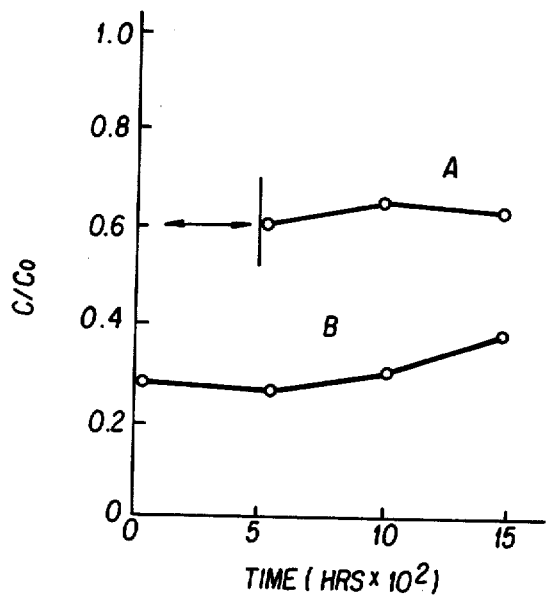
FIG. 11 is a diagram to illustrate the dependence of the bromine impregnation ratio on the thickness of the layer of the hydrogen bromide or hydrobromic acid-impregnated activated carbon in an apparatus of the embodiment shown in FIG. 10 when an acidic gas such as hydrogen sulfide is pretreated with sodium iodide-impregnated activated carbon or when it is not pretreated.

In FIG. 11, there is shown the dependence of bromine impregnation ratio of an old HBr-impregnated activated carbon on the layer thickness when the bad smell air on a trickling filter to treat a domestic waste water is deodorized for approximately 1500 hours. The experiment was carried out using two reaction columns each having a diameter of 40φ; in one of them, an HBr-impregnated activated carbon having a size of 4–8 meshes was packed by 15 cm in height and in the other one, a KI-impregnated activated carbon was packed at first by 5 cm in height to provide a space for adding ozone, then an HBr-impregnated activated carbon was packed by 10 cm in height. The diagram shows the results when the flow rate of the gas to be treated was 10 l/min., respectively, and ozone was added to the air at the inlet side of the packed layer of each HBr-impregnated activated carbon so that the concentration of ozone after dilution by the gas to be treated is 3 ppm. In this diagram, the characteristic curve A shows the dependence of bromine impregnation ratio on the layer thickness when the gas was allowed to pass through the KI-impregnated activated carbon being followed by addition of ozone and then the layer of HBr-impregnated activated carbon; the characteristic curve B shows the result when the bad smell air to which ozone was added was allowed to pass through only the packed layer of HBr-impregnated activated carbon. The bromine impregnation ratio of the HBr-impregnated activated carbon used was 0.8 wt.%. When hydrogen sulfide was removed by allowing the gas to pass through the KI-impregnated activated carbon, the bromine impregnation ratio was 0.6–0.65% maintaining considerably high levels; however, when the gas is not allowed to pass through the KI-impregnated activated carbon beforehand, the bromine impregnation ratio was 0.25–0.3% at the packed part of inlet side showing a remarkable decrease. Also the pH at a part less than 2 cm before the inlet side of the gas to be treated in the HBr-impregnated activated carbon was determined in accordance with the method of JIS K 1474. When the gas was allowed to pass through the KI-impregnated activated carbon, pH was 2.1 and when the gas was not allowed to pass through the KI-impregnated activated carbon, pH was 1.4 showing a high acidity; the detected value of sulfuric acid group was 5.6%. The pH of adjusted HBr-impregnated activated carbon was 2.4; accordingly, it is considered that, when the gas is not allowed to pass through the KI-impregnated activated carbon, the accumulation of sulfuric acid group was remarkable resulting in a remarkable lowering of pH of the HBr-impregnated activated carbon. Also the deodorization performance of pH of the HBr-impregnated activated carbon was higher when the KI-impregnated activated carbon was combined; in this case, the breakthrough of hydrogen sulfide was not observed (the concentration thereof was less than 5% of that at the inlet); however, a complete breakthrough was observed when the air to be treated to which ozone was added was allowed to pass through only the packed layer of HBr-impregnated activated carbon. Consequently, when a bad smell gas containing hydrogen sulfide of high concentration is treated, it is considered that, when hydrogen sulfide was removed by pretreatment and ozone was added thereto, the accumulation of sulfuric acid is controlled, the replacement of HBr with sulfuric acid being suppressed, the bromine impregnation ratio decreasing slowly, the deodorization performance being able to be maintained for a long time.

The KI-impregnated activated carbon mentioned in this embodiment was prepared by immersing the crushed coconut activated carbon in a 4% aqueous solution of potassium iodide for 30 minutes and then drying it in nitrogen gas. The amount of iodine impregnated was 0.9% as $I_2$. When an aqueous solution of KI having a concentration higher than 20% is used, the cost of chemicals exceeds 50% of the cost of the impregnated activated carbon causing an economical problem; accordingly, it is preferable that the impregnation ratio is in a range of 0.5–5%. The amount impregnated was determined by immersing the KI-impregnated activated carbon in hot water to extract the iodide and then titrating it in accordance with mercuric nitrate method.

Herein the effect of KI-impregnated activated carbon was explained; however, similar effect is revealed when an alkali metal or an alkali earth metal iodide is used. Also as a carrier other than an activated carbon, an activated clay, silica-alumina or alumina may be used.

Further, the case wherein an activated carbon is used as an agent to decompose excess oxidizing agent is shown in this example. However, similar effect is revealed when an alkali-impregnated porous material prepared by allowing a carrier such as an activated carbon, an activated clay, silica-alumina or alumina to impregnate an alkali such as sodium hydroxide, potassium hydroxide, sodium carbonate or potassium carbonate is used, and also a chemical adsorption of sulfur dioxide gas produced is possible.

As mentioned above in detail, the apparatus of this embodiment has a constitution that a gas to be treated is allowed to pass through the packed layer of $I_2$-impregnated porous material wherein acidic components such as hydrogen sulfide and methyl mercaptan are removed being followed by addition of ozone, the layer of HBr-impregnated porous material and further the layer of an activated carbon or the like which is an agent to decompose an oxidizing agent and the gas is discharged out of the system. Therefore, the accumulation of sulfuric acid in the HBr-impregnated porous material and the diffusion of HBr impregnated can be suppressed; consequently, $Br_2$ produced by the reaction of ozone and HBr can be effectively used and the components such as ammonia, dimethylsulfide and dimethyl disulfide which are not easily removed by adsorption with an activated carbon can be effectively removed. Also the apparatus reveals outstanding effects in practice, for instance, that no secondary environmental pollution takes place because the residual ozone and gaseous bromine contained in the air treated from which bad smell components were removed are adsorbed and removed by an activated carbon.

We claim:
1. A dry deodorizing apparatus comprising:
   (i) a device to diffuse ozonized air into odorous air containing bad smell components;
   (ii) a dry packed layer of a porous carrier into which a bromine compound is impregnated;
   (iii) a packed layer of an activated carbon; and
   (iv) means for allowing said odorous air to which ozone is added to first pass through said impregnated carrier and then through said layer of activated carbon.
2. The dry deodorizing apparatus of claim 1 wherein said porous carrier is an activated carbon, an activated clay, zeolite, silica-alumina or alumina.
3. The dry deodorizing apparatus of claim 1 wherein the amount of said bromine compound is in a range of about 0.1–10 wt.% as bromine per unit weight of the carrier.
4. The dry deodorizing apparatus of claim 3 wherein said range is from about 0.5–5 wt.%.
5. A dry deodorizing apparatus, comprising:
   (i) a device to diffuse ozonized air into odorous air containing bad smell components;
   (ii) a dry packed layer of a porous carrier into which a bromine compound is impregnated;
   (iii) a packed layer of a porous material into which an iodide of an alkali metal or an alkali earth metal is impregnated; and
   (iv) means for allowing said odorous air to which ozone is added to first pass through said carrier and then through the iodide-impregnated porous material.
6. The dry deodorizing apparatus of claim 5 wherein the amount of said alkali metal or alkali earth metal iodide is in a range of about 0.1–10 wt.% per unit weight of the porous material.
7. The dry deodorizing apparatus of claim 6 wherein said range is from about 0.5–5 wt.%.
8. A dry deodorizing apparatus, comprising:
   (i) a device to diffuse ozonized air into odorous air containing bad smell components;

(ii) a dry packed layer of a porous carrier into which a bromine compound is impregnated;

(iii) a packed layer of a porous material into which a bromide of an alkali metal or an alkali earth metal is impregnated;

(iv) a packed layer of an activated carbon; and means for allowing said odorous air to which ozone is added to first pass through said packed carrier then through said porous material and then through said layer of activated carbon.

9. The dry deodorizing apparatus of claim 8 which further comprises a blower upstream of the device for diffusing said ozonized air.

10. The dry deodorizing apparatus of claim 8 wherein the amount of said bromide is in a range of about 0.1-10 wt.% per unit weight of said porous material.

11. The dry deodorizing apparatus of claim 10 wherein said range is from about 0.5-5 wt.%.

12. A dry deodorizing apparatus, comprising:
(i) a device to diffuse ozonized air into odorous air containing bad smell components;
(ii) a dry packed layer of a porous carrier into which a bromine compound is impregnated;
(iii) a packed layer of a porous material into which a bromide of an alkali metal or an alkali earth metal is impregnated;
(iv) a packed layer of an alkali-impregnated porous substance; and means for allowing said odorous air to which ozone is added to first pass through said packed carrier then through said porous material and then through said layer of an alkali-impregnated porous substance.

13. The dry deodorizing apparatus of claim 12 wherein said alkali in alkali-impregnated porous substance is selected from the group consisting of alkali metal or alkali earth metal hydroxide and carbonate.

14. A dry deodorizing apparatus comprising:
(i) a packed layer of porous material into which an iodide of an alkali metal or an alkali earth metal is impregnated;
(ii) a device to diffuse ozonized air fed from said device into odorous air containing bad smell components which first passed through said packed layer of iodide-impregnated porous material;
(iii) a dry packed layer of a carrier into which a bromine compound is impregnated;
(iv) a packed layer of an agent which decomposes excess oxidizing agent; and
(v) means for allowing said odorous air to to first pass through said porous material to which ozone is added, then through said carrier and then through said layer of an agent which decomposes excess oxidizing agent.

15. The dry deodorizing apparatus of claim 14 wherein said agent for decomposing excess oxidizing agent is an activated carbon.

16. The dry deodorizing apparatus of claim 15 wherein said alkali is selected from the group consisting of sodium hydroxide, potassium hydroxide, sodium carbonate, potassium carbonate and mixtures thereof.

17. The dry deodorizing apparatus of claim 14 wherein said agent for decomposing excess oxidizing agent is an alkali-impregnated porous material.

18. The dry deodorizing apparatus of claim 17 wherein said alkali-impregnated porous material is an activated carbon, an activated clay, silica-alumina or alumina.

* * * * *